US010876051B2

(12) United States Patent
Cotte et al.

(10) Patent No.: US 10,876,051 B2
(45) Date of Patent: Dec. 29, 2020

(54) PROCESS AND DEVICE FOR SEPARATING AROMATICS UNDER VACUUM

(71) Applicant: Axens, Rueil-Malmaison (FR)

(72) Inventors: Arnaud Cotte, Nanterre (FR); Jérôme Pigourier, Meudon (FR); Nicolas Pupat, Houilles (FR)

(73) Assignee: AXENS, Rueil-Malmaison (FR)

( * ) Notice: Subject to any disclaimer, the term of this patent is extended or adjusted under 35 U.S.C. 154(b) by 0 days.

(21) Appl. No.: 16/401,171

(22) Filed: May 2, 2019

(65) Prior Publication Data
US 2019/0338196 A1 Nov. 7, 2019

(30) Foreign Application Priority Data

May 4, 2018 (FR) ..................................... 18 53884

(51) Int. Cl.
*C07C 7/00* (2006.01)
*C10G 7/06* (2006.01)
*C07C 7/04* (2006.01)

(52) U.S. Cl.
CPC ................ *C10G 7/06* (2013.01); *C07C 7/005* (2013.01); *C07C 7/04* (2013.01); *C10G 2300/20* (2013.01); *C10G 2400/30* (2013.01)

(58) Field of Classification Search
CPC ....... C07C 15/08; C07C 5/2737; C07C 7/005; C07C 7/08; C07C 7/12; B01D 1/28; B01D 1/2856; B01D 3/007; B01D 3/146
See application file for complete search history.

(56) References Cited

U.S. PATENT DOCUMENTS

2012/0048711 A1\* 3/2012 Werba .................... B01D 3/007
202/158
2015/0336023 A1 11/2015 Dunet et al.

FOREIGN PATENT DOCUMENTS

FR 2 998 301 A1 5/2014
FR 2 998 301 B1 1/2016

OTHER PUBLICATIONS

Preliminary Search Report for FR 18/53.884, dated Feb. 18, 2019.
G. Faagau: "Reduce column energy consumption", Chemical Processing, Jul. 16, 2008 (Jul. 16, 2008), XP002789023, Extrait de l'Internet: URL:https://www.chemicalprocessing.com/articles/2008/123/.
Everest Blowers: "Efficient Vacuum distillation" Jan. 2012 (Jan. 2012), XP002789024, pp. 1-9.

\* cited by examiner

*Primary Examiner* — Sharon Pregler
(74) *Attorney, Agent, or Firm* — Fitch, Even, Tabin & Flannery, LLP

(57) ABSTRACT

The present invention relates to a process and a device for separating a feedstock comprising benzene, toluene and C8+ compounds, by means of at least one "reformate" distillation column (C1), one aromatics extraction unit (P1), one para-xylene separation unit (P2), one xylene isomerization unit (P3) and one transalkylation unit (P4), the effluents of said units being separated in the following distillation columns: purification column (C6), deheptanizer (C7) and toluene column (C10), in which at least one of said distillation columns is suitable for being operated under vacuum so that: the majority of the C7− compounds are recovered in the product at the top of the distillation column operated under vacuum, and the majority of the C8+ compounds are recovered in the product at the bottom of the distillation column operated under vacuum.

15 Claims, 1 Drawing Sheet

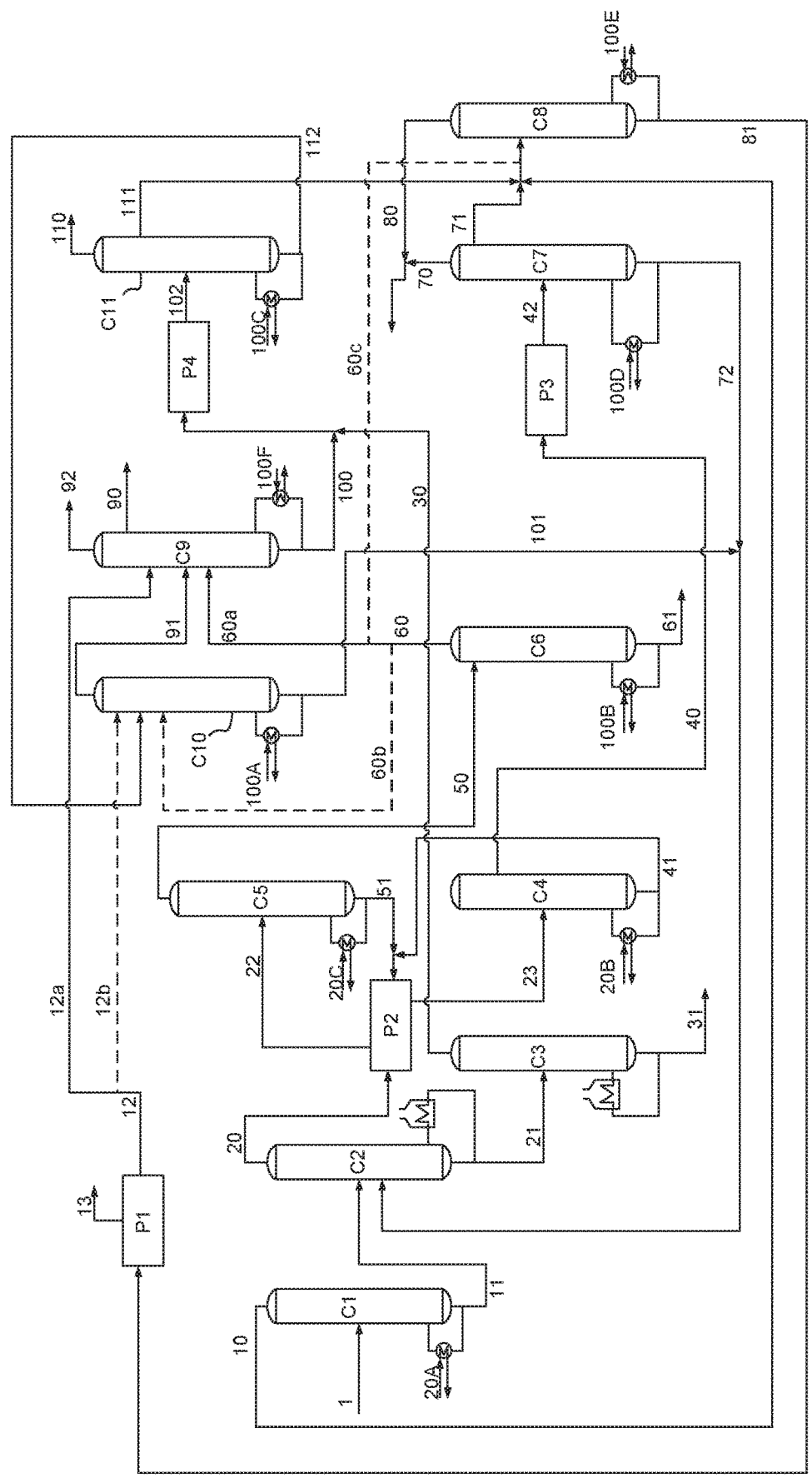

PROCESS AND DEVICE FOR SEPARATING AROMATICS UNDER VACUUM

TECHNICAL FIELD

The present invention falls in the field of processes and devices for separating aromatic compounds. The subject of the present invention applies in particular to the case of an aromatic complex which makes use of a separation by distillation between benzene and/or toluene and heavier compounds comprising 8 carbon atoms or more (hereinafter denoted C8+ compounds).

PRIOR ART

Patent FR 2 998 301 B1 describes a method which allows an overall energy saving in terms of fuel and electricity consumption of an aromatic complex for separation by distillation between benzene, toluene and C8+ compounds. Specifically, the principle of said method lies in the recovery of heat considered to be lost due to its low temperature level (around 100° C. to 180° C.) by generating low-pressure vapour in certain columns, the low-pressure vapour thus generated being used as a heat transfer fluid in the reboilers of certain columns and/or certain preheaters used in said method. This allows, for an aromatic complex, a substantial overall energy saving in terms of fuel and electricity consumption.

One drawback of patent FR 2 998 301 B1 is that recompression of the low-pressure vapour before use as a heat transfer fluid in the reboilers is required on a vast majority of the columns. Indeed, according to Table 2 of patent FR 2 998 301 B1, five columns use the low-pressure vapour produced within the complex, but only the stripper does so without recompression.

SUMMARY

In the context described above, a first object of the present invention is to enable a reduction in the amount of energy required to carry out the separation between benzene and/or toluene and C8+ compounds. Specifically, the first object consists in operating, under vacuum, columns of an aromatic complex which are usually operated under pressure. According to one or more embodiments, it is possible to perform a direct exchange between the low-temperature energy-producing and -consuming columns. The direct exchange may be replaced with a generation of low-pressure steam by the low-temperature heat-producing columns and use by the columns operated under vacuum, without recompression of this steam.

According to a first aspect, the abovementioned object, and also other advantages, are obtained by means of a process for separating a feedstock comprising benzene and/or toluene and compounds comprising 8 carbon atoms or more, in a separation device comprising at least one "reformate" distillation column, one aromatics extraction unit, one para-xylene separation unit, one xylene isomerization unit and one transalkylation unit, the effluents from said units being separated in the following distillation columns: purification column, deheptanizer and toluene column, in which at least one of said distillation columns is operated under vacuum so that:
the majority of the compounds comprising 7 carbon atoms or less are recovered in the top of the distillation column operated under vacuum, and
the majority of the compounds comprising 8 carbon atoms or more are recovered in the product at the bottom of the distillation column operated under vacuum.

According to one or more embodiments, the product at the bottom of the distillation column operated under vacuum has a content of greater than 25% (preferably 35% by weight and even more preferably 50% by weight) of compounds comprising 8 carbon atoms and/or compounds of which the normal boiling point is less than 150° C.

According to one or more embodiments, the pressure at the column top of the distillation column operated under vacuum is between 0.03 MPa and 0.095 MPa (preferably between 0.04 MPa and 0.085 MPa and even more preferably between 0.05 and 0.075 MPa).

According to one or more embodiments, the reboiler of the distillation column operated under vacuum is operated at a temperature of less than 180° C. (preferably less than 165° C. and even more preferably less than 150° C.).

According to one or more embodiments, a low-temperature heat is introduced into the reboiler of the distillation column operated under vacuum, from low-temperature energy available in the separation device, either by direct exchange, or by means of the generation of steam used without recompression.

According to one or more embodiments, the C4− content in the product at the top of the distillation column operated under vacuum is less than 1 mol % (preferably less than 0.5 mol % and even more preferably less than 0.1 mol %).

According to one or more embodiments, the product at the top of the distillation column operated under vacuum is directed to an additional column comprising, at the top of the column, a vapour stream bled off out of the separation process (preferably for bleeding off oxygen with the vapour stream bled off at the column top of the additional column).

According to one or more embodiments, the reboiler of the additional column is operated at a temperature of less than 180° C. (preferably by direct exchange or using an intermediate heat-transfer fluid which does not require recompression).

According to a second aspect, the abovementioned object, and also other advantages, are obtained by means of a device for separating a feedstock comprising benzene, toluene and compounds comprising 8 carbon atoms or more, comprising at least one "reformate" distillation column, one aromatics extraction unit, one para-xylene separation unit, one xylene isomerization unit and one transalkylation unit, the separation device also comprising the following columns for the distillation of the effluents from said units: purification column, deheptanizer and toluene column, in which at least one of said distillation columns is suitable for being operated under vacuum so that:
the majority of the compounds comprising 7 carbon atoms or less are recovered in the top of the distillation column operated under vacuum, and
the majority of the compounds comprising 8 carbon atoms or more are recovered in the product at the bottom of the distillation column operated under vacuum.

According to one or more embodiments, the at least one of said distillation columns is adapted so that the product at the bottom of the distillation column operated under vacuum has a content of greater than 25% by weight (preferably 35% by weight and even more preferably 50% by weight) of compounds comprising 8 carbon atoms and/or compounds of which the normal boiling point is less than 150° C.

According to one or more embodiments, the at least one of said distillation columns is adapted so that the pressure at the column-top of the distillation column operated under vacuum is between 0.03 MPa and 0.095 MPa (preferably between 0.04 MPa and 0.085 MPa and even more preferably between 0.05 and 0.075 MPa).

According to one or more embodiments, the at least one of said distillation columns is adapted so that the reboiler of the distillation column operated under vacuum is operated at a temperature of less than 180° C. (preferably less than 165° C. and even more preferably less than 150° C.).

According to one or more embodiments, the at least one of said distillation columns is adapted so that the reboiler of the distillation column operated under vacuum can be supplied with a low-temperature heat originating from low-temperature energy available in the complex, either by direct exchange, or by means of the generation of steam used without recompression.

According to one or more embodiments, the at least one of said distillation columns is adapted so that the content of C4− (compounds comprising 4 carbon atoms or less) in the product at the top of the distillation column operated under vacuum is less than 1 mol % (preferably less than 0.5 mol % and even more preferably less than 0.1 mol %).

According to one or more embodiments, the separation device also comprises an additional column, downstream of the outlet at the top of the distillation column operated under vacuum, for bleeding off a vapour stream at the top of the column out of the separation device (preferably for breeding off oxygen with the vapour stream bled off at the column-top of the additional column).

According to one or more embodiments, the additional column is adapted so that the reboiler of the additional column is operated at a temperature of less than 180° C. (preferably by direct exchange or using an intermediate heat-transfer fluid which does not require recompression).

Embodiments of the process and of the device referred to above and also other features and advantages will become apparent on reading the description that follows, given solely by way of illustration and in a non-limiting manner, and with reference to the following drawing.

BRIEF DESCRIPTION OF THE DRAWING

FIG. 1 describes a scheme of an aromatic complex according to the present invention for the separation of benzene and/or of toluene and of C8+ compounds, in which at least one of the distillation columns is operated under vacuum.

DETAILED DESCRIPTION

The present invention relates to the field of processes and devices for separating a feedstock comprising benzene and/or toluene and C8+ (e.g. C8 to C10) compounds which may in particular comprise para-xylene.

The separation process and device according to the present invention can be defined as a series of conversion and separation steps and sections which is intended to separate benzene and toluene from C8+ compounds and in particular from aromatic compounds comprising eight carbon atoms, known as xylenes, and more particularly para-xylene, starting from a feedstock rich in aromatic compounds ranging from benzene to aromatic compounds comprising more than 10 carbon atoms (denoted C10+), originating for example from a catalytic reforming unit. The feedstock rich in aromatic compounds typically has contents of sulfur-containing compounds, nitrogenous compounds and olefin compounds that are very low to zero (e.g. sulfur content <0.5 ppm by weight and/or nitrogen content <0.5 ppm by weight and/or a bromine number <1 g/100 g according to ASTM D1159), since these compounds can affect the performance and the lifetime of certain catalysts and molecular sieves used in the aromatic complex units.

The first subject of the present invention can be defined as the operation under vacuum of distillation columns so that:
the majority of the compounds comprising 8 carbon atoms (e.g. xylenes) or more are recovered in the bottom product, and
the majority of the aromatic compounds comprising 7 carbon atoms (e.g. toluene) or less (e.g. benzene) are recovered in the top product.

According to one or more embodiments, the content of compounds comprising 8 carbon atoms (or compounds of which the normal boiling point is less than 150° C.) in the bottom product is greater than 25% by weight (preferably 35% by weight and even more preferably 50% by weight).

According to one or more embodiments, the C4− content in the top product is less than 1 mol % (even more preferably 0.5 mol % and even more preferably 0.1 mol %).

Such a distillation column makes it possible, if it is operated under vacuum (e.g. at a pressure below atmospheric pressure):
to have a reboiler temperature at the bottom of less than 180° C. (preferably less than 165° C. and more preferably less than 150° C.) since a large fraction of the bottom product consists of compounds of which the normal boiling point is less than 150° C.; and
to be able to condense, at the top of said distillation column operating under vacuum, virtually all of the C5-C7 fraction at temperatures compatible with the cooling water available in the refinery. Specifically, the lightest of the C5+ compounds, isopentane, has a normal boiling point equal to 20° C. and a bubble point of 20° C. at 0.08 MPa.

Furthermore, when the content of light compounds in the product at the top (C4−) is low (C4− content of less than 1 mol %, even more preferably 0.5 mol % and even more preferably 0.1 mol %), the distillation column operated under vacuum can be operated under vacuum without generating, at the top, a significant vapour phase that will have to be re-compressed by a compressor. According to one or more embodiments, only a small flow of uncondensable compounds, in particular those linked to a possible air inlet in a system under vacuum, is to be taken up by usual means on a vacuum distillation column, namely an ejector or vacuum pump.

According to one or more embodiments, the pressure at the top of the distillation column operated under vacuum (in the pipe at the top of the shell of said column) is between 0.03 MPa and 0.095 MPa, preferably between 0.04 MPa and 0.085 MPa, and even more preferably between 0.05 and 0.075 MPa.

According to one or more embodiments, the distillation column operated under vacuum is reboiled by energy with a low thermal level (e.g. at a temperature of less than 180° C.) available in the complex. Said column may for example be reboiled either directly by the low-temperature heat source (<180° C.), or by means of low-pressure vapour but without requiring recompression thereof as in the reference processes.

Since the operation of a vacuum distillation column may involve a low input of air and therefore of oxygen into the separation process and device and the presence of oxygen may prove to be harmful, in particular by possible poisoning of the catalysts downstream, the product at the top of the distillation column operated under vacuum can be directed to an additional column comprising, at the top of the column, a vapour stream that will be bled off out of the process. According to one or more embodiments, a column that already exists in the separation process and device is used to bleed off the oxygen in the vapour stream at the top of this additional column. For example, the stripper can be used to bleed off the oxygen from the products at the top of the reformate column and/or of the deheptanizer and/or of the purification column (e.g. in the case where the benzene column is not used); the benzene column can be used to bleed off the oxygen from the products at the top of the purification column and/or of the toluene column.

Since the feedstock of the additional column is depleted of C8+ compounds and since it very predominantly consists of C7-compounds (and/or compounds with a normal boiling point of less than 120° C.), the additional column can be reboiled by energy with a low thermal level (e.g. at a temperature of less than 180° C.), for example:

by direct exchange; or
using an intermediate heat-transfer fluid, such as low-pressure vapour (not requiring recompression).

In the description which follows, the term "complex" is used to denote any refining or petrochemical device comprising at least two distillation columns. This definition is very broad and comprises, for example, the device for catalytic cracking of petrols and the device for producing para-xylene or meta-xylenes from aromatic fractions termed "aromatic complex". The description which follows and the example which illustrates the separation process and device according to the present invention are given in the case of an aromatic complex, but it is clearly understood that an aromatic complex does not constitute only one case of application and in no way limits the scope of the separation process and device disclosed in the present description.

FIG. 1 describes a scheme of a separation process and device according to one or more embodiments of the present invention, making it possible in particular to reduce the energy consumption required for separation between benzene, toluene and C8+ compounds compared to the reference process and aromatic complex.

With reference to FIG. 1, in particular described are zones of the separation process and device suitable for operating under vacuum at least one of said distillation columns (C1, C6, C7 and C10) so that the majority of the compounds comprising 7 carbon atoms or less are recovered in the product at the top of the distillation column operated under vacuum, and the majority of the compounds comprising 8 carbon atoms or more are recovered in the product at the bottom of the distillation column operated under vacuum.

According to one or more embodiments, the reformate column and the toluene column are suitable for being operated under vacuum. According to one or more embodiments, the purification column and the toluene column are suitable for being operated under vacuum. According to one or more embodiments, the reformate column, the purification column and the toluene column are suitable for being operated under vacuum. According to one or more embodiments, the reformate column, the purification column, the deheptanizer and the toluene column are suitable for being operated under vacuum.

The conversion and separation steps and sections of the separation process and device of the present invention are described in greater detail below.

Reformate Column C1

The feedstock to be treated is sent, via the line 1, to the first distillation column, denoted reformate column C1, which separates the toluene and the lighter compounds (fraction of C7− compounds) from the heavier compounds (fraction of C8 to C10+ compounds).

According to one or more embodiments, the reformate column C1 is operated under vacuum so as to have a temperature of less than 180° C. (e.g. <165° C.) in the reboiler 20A. According to one or more embodiments, the reformate column C1 is operated under vacuum so as to have a temperature of less than 150° C. in the reboiler 20A. Thus, the reformate column C1 can be reboiled by low-temperature energy (<180° C.).

In FIG. 1, the effluent at the top of the reformate column C1 is directed to the stripping column C8 (via line 10). According to one or more embodiments, the top of the reformate column C1 thus performs a passage through the stripping column C8 before rejoining the aromatics extraction unit P1 (via the line 81).

In the reference processes and aromatic complexes, the effluent at the top of the reformate column C1 is directed to the aromatics extraction unit P1.

Although the energy balance is less advantageous, according to one or more embodiments, at least one portion of the effluent at the top of the reformate column C1 can be directly directed to the aromatics extraction unit P1. According to one or more embodiments, when the reformate column C1 is not operated under vacuum, at least one portion of the effluent at the top of the reformate column C1 can be directly directed to the aromatics extraction unit P1. These embodiments are employed for example.

According to one or more embodiments, the lightest compounds, such as oxygen, are bled off at the top of the stripping column C8. The bottom of the stripping column C8, preferably with the oxygen removed, is sent to the aromatics extraction unit P1.

Aromatics Extraction Unit P1

The toluene and the benzene and optionally the compounds recovered at the bottom of the stripper C8 are sent, via the line 81, to the aromatics extraction unit P1.

The aromatics extraction unit P1 separates the essentially aromatic C6-C7 fraction from a product comprising paraffin compounds which is sent out of the aromatic complex via the line 13. The solvent preferentially used in the aromatics extraction unit P1 is N-formylmorpholine (NFM).

With reference to FIG. 1, the C6-C7 fraction from the aromatics extraction unit P1 is directed, via the line 12, either to the benzene column C9 (line 12a), or in order to be purified of some C8 compounds that it might contain, to the toluene column C10 (12b).

According to one or more embodiments, the aromatics extraction unit P1 comprises an extractive distillation unit.

Xylene Column C2

The C8-C10+ aromatic compounds recovered at the bottom of the column C1 are sent, via the line 11, to the xylene column C2 in order to separate the C9 aromatic compounds and heavier compounds (C9+ compounds) from a xylene fraction comprising C8 aromatic compounds which supply the units of the aromatic complex that are located downstream.

According to one or more embodiments, the operating pressure at the top of the xylene column C2 is maintained at the minimum pressure required (generally of between 0.7 and 1.2 MPa absolute), which allows a vapour condensation temperature at the top of the xylene column C2 that is sufficient to be used as heat-transfer fluid for the reboilers (20B and 20C for example) of certain distillation columns (C4 and C5 for example).

Para-Xylene Separation Unit P2

The xylene fraction, that is to say the fraction of C8 aromatic compounds containing para-xylene, meta-xylene, ortho-xylene and ethylbenzene, is recovered at the top of the xylene column C2 and is sent, via the line 20, to the para-xylene separation unit P2 which selectively recovers the para-xylene contained in said xylene fraction.

Said para-xylene separation unit P2 may be a para-xylene adsorption unit suitable for producing a mixture of para-xylene and of desorbent (also known as the extract) and a mixture of the other aromatic C8– compounds and of desorbent (known as the raffinate).

The adsorbent used is a molecular sieve dedicated to the adsorption of para-xylene, that is to say that it has a particularly high affinity for this compound.

An adsorbent solid commonly used is a zeolite of faujasite type formed with a siliceous binder, exchanged with barium or with potassium. The desorbent preferentially used is para-diethylbenzene (PDEB).

According to one or more embodiments, the para-xylene separation unit P2 comprises a para-xylene crystallization unit, for example as described in U.S. Pat. No. 3,467,724.

According to one or more embodiments, the para-xylene separation unit P2 comprises a combination of a para-xylene adsorption unit and a crystallization unit as described in patent EP-B-053191.

Extract Column C5

This column is used when the para-xylene separation unit is of the para-xylene adsorption type. The stream of extract from the para-xylene adsorption unit and containing the para-xylene and desorbent is sent, via the line 22, to the extract column C5 which separates the para-xylene from the desorbent. The desorbent recovered at the bottom of the extract column C5 is sent back to the para-xylene adsorption unit P2 via the line 51. The para-xylene recovered at the top of the extract column C5 is sent to the purification column C6.

According to one or more embodiments, the extract column C5 is operated under a very slight pressure, in a pressure range of from 0.2 to 0.4 MPa absolute (in the reflux drum). This is so as to minimize both the temperature of the reboiler 20C and the amount of heat to be supplied to said reboiler 20C while at the same time making it possible to produce, via the condensation at the top, energy with a low thermal level (e.g. 150° C.-180° C.).

The condensation of the vapours at the top of the extract column C5, must be completely or partially carried out by means of a low-pressure vapour generation or by direct exchange with the reboiler of another column.

Purification Column C6

The stream at the top of the extract column C5 is sent, via line 50, to the purification column C6 which separates the toluene (that was partially extracted with the para-xylene) from the para-xylene.

The high-purity para-xylene produced is recovered at the bottom of the purification column C6 and conveyed as finished product by pumping for storage via line 61.

According to one or more embodiments, the purification column C6 is operated under vacuum so as to have a temperature of less than 180° C. (e.g. <165° C.) in the reboiler 100B. According to one or more embodiments, the purification column C6 is operated under vacuum so as to have a temperature of less than 150° C. in the reboiler 100B. Thus, the purification column C6 can be reboiled by low-temperature energy (<180° C.).

According to one or more embodiments, the product at the top of the purification column C6 is directed to the benzene column C9 (line 60a) which may comprise at the top of the column a vapour stream (92), consisting of uncondensable compounds, bled off out of the process.

According to one or more embodiments, the product at the top of the purification column C6 can be directed to the toluene column C10 (line 60b) in order to purify said top product of some C8 compounds that it might contain. According to one or more embodiments, the product at the top of the toluene column C10 is directed to the benzene column C9 which may comprise at the top of the column a vapour stream (92), consisting of uncondensable compounds, bled off out of the process.

According to one or more embodiments, the product at the top of the purification column C6 is directed to the stripping column C8 (line 60c) which may comprise at the top of the column a vapour stream, consisting of uncondensable compounds, bled off out of the process.

Raffinate Column C4

The raffinate originating from the para-xylene separation unit P2 is sent, by the line 23, to the raffinate column C4 which separates the aromatic C8 compounds (raffinate) from the desorbent. The desorbent recovered at the bottom of the raffinate column C4 is sent back to the para-xylene separation unit P2 via the line 41.

The raffinate (C8 aromatics fraction) is extracted by drawing off as a sidestream and sent, by the line 40, as feedstock for the xylene isomerization unit P3.

According to one or more embodiments, the raffinate column C4 is operated under a very slight pressure, in a pressure range of from 0.2 to 0.4 MPa absolute (in the reflux drum). This is so as to minimize both the temperature of the reboiler 20B and the amount of heat to be supplied to said reboiler 20B while at the same time making it possible to produce, via the condensation at the top, energy with a low thermal level (150° C.-180° C.).

The condensation of the vapours at the top of the raffinate column C4 can thus be completely or partially carried out by means of a low-pressure vapour generation or by direct exchange with the reboiler of another column.

Desorbent Column (not Represented)

This column is used when the para-xylene separation unit is of the para-xylene adsorption type. A small portion of the desorbent circulating in the para-xylene adsorption unit P2 is sent to the desorbent column (not represented) so as to eliminate there from the heavy compounds which otherwise would accumulate in the loop.

Xylene Isomerization Unit P3

The xylene isomerization unit P3 is used to convert a para-xylene-poor feedstock into a xylene stream at thermodynamic equilibrium (denoted isomerate).

Any type of catalyst capable of isomerizing hydrocarbons comprising 8 carbon atoms can be used in the separation process and device according to the present invention. A catalyst containing a dehydrogenating metal, such as platinum, palladium or nickel, and an acid phase, for example a doped alumina, a zeolite such as mordenite, MFI, zeolite Y or zeolite or non-zeolite molecular sieves comprising an acidity, such as aluminophosphates (e.g. aluminophosphates AlPO, silicoaluminophosphates SAPO), is preferably used. It is thus possible, more preferably, to use an isomerization catalyst comprising a zeolite of EUO structural type, such as the zeolite EUI, the zeolite ZSM 50 or the zeolite TPZ3 as described in U.S. Pat. No. 4,640,829, EP-B-042226 or EP-B-051318.

Deheptanizer C7

The effluent from the xylene isomerization unit P3 is sent, by the line 42, to the deheptanizer C7 which separates the isomer (aromatic C8+ compounds) from a C7− light fraction recovered at the top of said deheptanizer column C7. This C7− fraction is sent, by the line 71, to the stripper C8 in order to separate the light compounds from the C7 fraction.

The C8+ fraction, formed of xylenes and heavier compounds, recovered at the bottom of the deheptanizer C7 is recycled, by the line 72, to the xylene column C2.

According to one or more embodiments, the deheptanizer C7 is operated under vacuum so as to have a temperature of less than 180° C. (e.g. <165° C.) in the reboiler 100D. According to one or more embodiments, the deheptanizer C7 is operated under vacuum so as to have a temperature of less than 150° C. in the reboiler 100D. Thus, the deheptanizer C7 can be reboiled by low-temperature energy (<180° C.).

According to one or more embodiments, the product at the top (line 71) of the deheptanizer C7 operated under vacuum is then directed to the stripper C8 comprising at the column top a vapour stream (line 80), consisting of uncondensable compounds, bled off out of the process.

According to one or more embodiments, given the possibly high content of light compounds (C4−) in the deheptanizer (C7), the product at the top of the deheptanizer C7 may comprise a vapour phase 70 and a liquid phase 71 (both derived from the reflux drum).

Stripper C8

The stripper (or stripping column) C8 is supplied by the top of the deheptanizer C7.

The stabilized C7− fraction is recovered at the bottom of the stripper C8 to be sent to the aromatics extraction unit P1 via the line 81.

According to one or more embodiments, the stripper C8 is also supplied by the product at the top of the reformate column C1. The lightest compounds, such as air and/or oxygen resulting from the operation under vacuum of the reformate column C1, can be bled off at the top of the stripping column.

According to one or more embodiments, the stripper C8 is also supplied by the product at the top of the purification column C6. The lightest compounds, such as air and/or oxygen resulting from the operation under vacuum of the purification column C6, can be bled off at the top of the stripping column.

According to one or more embodiments, the stripper C8 comprises a reboiler 100E. The light compounds (C4−) from the top of the stripper C8 are mixed, by the line 80, with the light compounds from the top of the deheptanizer C7 and bled off.

Heavy Aromatics Column C3

The C9+ aromatic compounds recovered at the bottom of the xylene column C2 are sent, via the line 21, to the heavy aromatics column C3 which separates the C9 and C10 aromatic compounds from the heavier compounds (such as naphthalene) which may have an unfavourable effect on the transalkylation catalyst and which are recovered at the bottom by the line 31.

According to one or more embodiments, the heavy aromatics column C3 is operated at low pressure, in a pressure range of between 0.1 and 0.2 MPa absolute (in the reflux drum), so as to minimize both the temperature and the amount of heat to be introduced into the reboiler of said heavy aromatics column C3.

Transalkylation Unit P4

The C9 and C10 aromatic compounds recovered at the top of the heavy aromatics column C3 are sent, by the line 30, to the transalkylation unit P4.

With reference to FIG. 1, said C9 and C10 aromatic compounds are mixed with the toluene originating from the bottom of the benzene column C9 (line 100).

The transalkylation unit P4 converts the toluene and the C9+ aromatic compounds, originating from the reformate column C1 and from the isomerate of the xylene isomerization unit P3 (after passing through the xylene column C2 and the heavy aromatics column C3), into a mixture of xylenes and benzene via a thermodynamics-limited reaction.

Any type of transalkylation catalyst can be used in the separation process and device according to the present invention, for example catalysts based on mordenite or faujasite described in U.S. Pat. No. 3,437,710 or the catalysts based on MCM-22 or beta zeolites described in U.S. Pat. No. 5,030,787, or the catalysts based on mordenite and MFI zeolites as described in patent application US 2012/0065446. These catalysts generally additionally comprise a metal compound preferably chosen from the group formed by rhenium, nickel, cobalt, molybdenum, tungsten, palladium and platinum.

Stabilization Column C11

The effluent from the transalkylation unit P4 which contains benzene and xylenes and also toluene and unconverted C9+ compounds is sent, via the line 102, to the stabilization column C11 which separates the compounds that are lighter than benzene, from the benzene and the heavier aromatic compounds denoted C7+.

The gas leaving (the reflux drum of) the stabilization column C11 is sent, via the line 110, to the limit of the aromatic complex. An unpurified benzene fraction is drawn off as a side stream and sent, via the line 111, to the stripping column C8 which makes it possible to separate the light compounds from said fraction.

According to one or more embodiments, the partial condensation of the gases from the top of the stabilization column C11 is obtained by means of an air-cooled heat exchanger followed by a water cooler. According to one or more embodiments, the stabilization column C11 comprises a reboiler 100C.

Toluene Column C10

With reference to FIG. 1, the toluene column C10 is supplied by the C7+ fraction from the bottom of the stabilization column C11 (line 112).

According to one or more embodiments, the C6-C7 fraction from the aromatics extraction unit P1 is sent to the toluene column C10.

The product at the top of the toluene column C10 is a fraction rich in C7− compounds (e.g. essentially toluene+ C6− compounds) and the bottom product is a C8+ fraction rich in aromatic compounds comprising 8 carbon atoms.

The C8+ fraction extracted at the bottom of the toluene column C10 (i.e. product at the bottom of the toluene column C10 enriched with compounds comprising 8 carbon atoms or more) is recycled, via the line 101, to the xylene column C2 which separates the C9+ and heavier products from the C8 aromatics fraction supplying the separation device.

Since the effluent from the top of the purification column C6 may have a very low flow rate compared with the other two streams treated by the toluene and benzene columns, according to one or more embodiments of the present invention (not represented), said effluent is mixed with the C7+ fraction from the bottom of the column C11.

According to one or more embodiments, the toluene column C10 is operated under vacuum so as to have a temperature of less than 180° C. (e.g. <165° C.) in the reboiler 100A. According to one or more embodiments, the toluene column C10 is operated under vacuum so as to have a temperature of less than 150° C. in the reboiler 100A. Thus, the toluene column C10 can be reboiled by low-temperature energy (<180° C.).

According to one or more embodiments, the product at the top of the toluene column C10 is directed to the benzene column C9 comprising at the top of the column a vapour stream (line 92), consisting of uncondensable compounds, bled off out of the process.

Benzene Column C9

With reference to FIG. 1, the C7− fraction extracted at the top of the toluene column C10 (i.e. product at the top of the toluene column enriched with benzene and with toluene) is directed, via the line 91, to the benzene column C9.

According to one or more embodiments of the present invention, for example when the C6-C7 fraction from the aromatics extraction unit P1 contains very little C8+(for example <1% by weight of C8+ in the C6-C7 fraction, preferably <0.5% by weight and even more preferably <0.3% by weight), the C6-C7 fraction from the aromatics extraction unit P1 is directed to the benzene column C9 downstream of the toluene column (as a mixture with or separately from the top of the toluene column C10). According to one or more embodiments, the supplying of the benzene column C9 from the aromatics extraction unit P1 is carried out separately and preferably on top (downstream) of the supply from the top of the toluene column C10.

From the benzene column C9, the benzene-enriched top product is extracted as final product via the line 90. According to one or more embodiments, the benzene-enriched product is extracted by drawing off as a sidestream. According to one or more embodiments, light and uncondensable compounds, in particular those resulting from the air intake linked to the vacuum operation of the toluene column (C10) and/or the purification column (C6), are bled off via a vapour stream at the column top (line 92). The toluene-enriched product at the bottom of the benzene column C9 is directed, via the line 100, to the transalkylation unit P4.

According to one or more embodiments, the benzene column C9 is operated at low pressure, in a pressure range of from 0.1 to 0.2 MPa absolute (in the reflux drum), so as to minimize both the temperature and the amount of heat to be introduced into the reboiler 100F. Thus, the benzene column C9 can be reboiled by low-temperature energy (e.g. <180° C.).

In FIG. 1, in the interests of simplification, the optional reflux, reflux drum, condenser and vacuum system sections are not represented; any known condensation means (for example: air-cooled heat exchanger and/or water cooler) may be used.

EXAMPLE

In the example:
the product at the top of the reformate column C1 is sent to the stripper C8, from where the compounds resulting from an intake of air into the column C1 will be bled off at the top;
the product at the top of the toluene column C10 is sent to the benzene column C9, from where the compounds resulting from an intake of air into the column C10 will be bled off at the top; and
the product at the top of the purification column C6 is sent to the benzene column C9, from where the compounds resulting from an intake of air into the column C6 will be bled off at the top.

The compositions of the feedstock and of the products of the reformate column C1 are indicated in Table 1.

TABLE 1

|  |  | C1 feedstock | C1 bottom product | C1 top product |
|---|---|---|---|---|
| C4− | kg/hr | 0 | 0 | 0 |
| C5 | kg/hr | 4142 | 0 | 4142 |
| C6 Non-aromatic | kg/hr | 4570 | 0 | 4570 |
| C6 Aromatic | kg/hr | 9298 | 0 | 9298 |
| C7 Non-aromatic | kg/hr | 4042 | 0 | 4042 |
| C7 Aromatic | kg/hr | 44 891 | 449 | 44 442 |
| C8 Non-aromatic | kg/hr | 571 | 27 | 544 |
| C8 Aromatic | kg/hr | 48 033 | 47 793 | 240 |
| C9+ | kg/hr | 27 452 | 27 452 | 0 |
| TOTAL | kg/hr | 142 999 | 75 721 | 67 279 |

As indicated in Table 2, the conditions previously indicated so that, according to the invention, the reformate column C1 can be operated under vacuum, are met:

TABLE 2

| Degree (by weight) of recovery of C8+ compounds at the bottom | 99% |
|---|---|
| Degree (by weight) of recovery of C7− compounds at the top | 99.3% |
| C8 content at the bottom | 63.2% by weight |

Moreover, the content of light (C4−) compounds is less than 0.1% by weight.

The reformate column C1 operated at 40° C. and 0.05 MPa abs at the top has a temperature of approximately 135° C. in the reboiler 20A.

The compositions of the feedstock and of the products of the toluene column C10 are indicated in Table 3.

TABLE 3

|  |  | C10 feedstock | C10 bottom product | C10 top product |
|---|---|---|---|---|
| C4− | kg/hr | 0 | 0 | 0 |
| C5 | kg/hr | 0 | 0 | 0 |
| C6 Non-aromatic | kg/hr | 27 | 0 | 27 |
| C6 Aromatic | kg/hr | 12 297 | 0 | 12 297 |
| C7 Non-aromatic | kg/hr | 15 | 0 | 15 |
| C7 Aromatic | kg/hr | 62 585 | 259 | 62 326 |
| C8 Non-aromatic | kg/hr | 1 | 0 | 1 |
| C8 Aromatic | kg/hr | 52 083 | 51 822 | 260 |
| C9+ | kg/hr | 18 682 | 18 682 | 0 |
| TOTAL | kg/hr | 145 690 | 70 763 | 74 926 |

As indicated in Table 4, the conditions previously indicated so that, according to the invention, the toluene column C10 can be operated under vacuum, are met:

TABLE 4

| Degree (by weight) of recovery of C8+ compounds at the bottom | 99.6% |
|---|---|
| Degree (by weight) of recovery of C7− compounds at the top | 99.7% |
| C8 content at the bottom | 73.2% by weight |

Moreover, the content of light (C4−) compounds is less than 0.1% by weight.

The toluene column C10 operated at 40° C. and 0.05 MPa abs at the top has a temperature of approximately 135° C. in the reboiler 100A.

The compositions of the feedstock and of the products of the purification column C6 are indicated in Table 5.

TABLE 5

|  |  | C6 feedstock | C6 bottom product | C6 top product |
|---|---|---|---|---|
| C4− | kg/hr | 0 | 0 | 0 |
| C5 | kg/hr | 0 | 0 | 0 |
| C6 Non-aromatic | kg/hr | 0 | 0 | 0 |
| C6 Aromatic | kg/hr | 124 | 0 | 124 |
| C7 Non-aromatic | kg/hr | 0 | 0 | 2 |
| C7 Aromatic | kg/hr | 1159.5 | 4.5 | 1155.0 |
| C8 Non-aromatic | kg/hr | 0 | 0 | 0 |
| C8 Aromatic | kg/hr | 90 361 | 90 335 | 26 |
| C9+ | kg/hr | 18 | 18 | 0 |
| TOTAL | kg/hr | 91 662.5 | 90 357.5 | 1307.0 |

As indicated in Table 6, the conditions previously indicated so that, according to the invention, the purification column C6 can be operated under vacuum, are met:

TABLE 6

| | |
|---|---|
| Degree (by weight) of recovery of C8+ compounds at the bottom | 99.97% |
| Degree (by weight) of recovery of C7− compounds at the top | 99.8% |
| C8 content at the bottom | 99.98% by weight |

Moreover, the content of light (C4−) compounds is less than 0.1% by weight.

The purification column C6 operated at 40° C. and 0.06 MPa abs at the top has a temperature of approximately 130° C. in the reboiler 100B.

The operation under vacuum of these three distillation columns (C1, C10 and C6) allows, on the scale of the complex, a reduction in electrical consumption of 46% compared with the reference processes and devices. The reduction in electrical consumption is in particular due to the fact that it is no longer necessary to recompress the low-pressure vapour resulting from the low-temperature energy available in the aromatic complex before it is used to reboil these three distillation columns (C1, C10 and C6).

If the invention is applied to only one of the 3 columns, the following results are obtained.

15% gain compared with the reference processes and devices for solely the reformate column C1,
20% gain compared with the reference processes and devices for solely the toluene column C10,
11% gain compared with the reference processes and devices for solely the purification column C6.

The invention claimed is:

1. A process for separating a feedstock comprising benzene and/or toluene and compounds comprising 8 carbon atoms or more, in a separation device comprising at least one "reformate" distillation column (C1), an aromatics extraction unit (P1), a para-xylene separation unit (P2), a xylene isomerization unit (P3) and a transalkylation unit (P4), the effluents from the aromatics extraction unit (P1), the para-xylene separation unit (P2), the xylene isomerization unit (P3) and the transalkylation unit (P4) being separated in at least one of a purification column (C6) and a toluene column (C10),
in which at least one of the "reformate" distillation column (C1), the purification column (C6, C7) and the toluene column (C10) is operated under vacuum so that:
the majority of the compounds comprising 7 carbon atoms or less are recovered in the top of the column operated under vacuum, and
the majority of the compounds comprising 8 carbon atoms or more are recovered in the product at the bottom of the column operated under vacuum, and
in which the product at the top of the column operated under vacuum is directed to an additional column comprising, at the top of the column, an oxygen stream bled off out of the process for separating the feedstock.

2. The process according to claim 1, in which the distillation column is operated under vacuum so that the product at the bottom of the distillation column operated under vacuum has a content of greater than 25% by weight of compounds comprising 8 carbon atoms and/or compounds of which the normal boiling point is less than 150° C.

3. The process according to claim 1, in which the pressure at the column top of the distillation column operated under vacuum is between 0.03 MPa and 0.095 MPa.

4. The process according to claim 1 in which the reboiler of the distillation column operated under vacuum is operated at a temperature of less than 180° C.

5. The process according to claim 1, in which the distillation column operated under vacuum is operated so that the C4− content in the product at the top of the distillation column operated under vacuum is less than 1 mol %.

6. The process according to claim 1, in which the reboiler of the additional column has a temperature of less than 180° C.

7. The process according to claim 1, in which a low-temperature heat is introduced into the reboiler of the distillation column operated under vacuum, from low-temperature energy available in the separation device, either by direct exchange, or by means of the generation of steam used without recompression.

8. A device for separating a feedstock comprising benzene and/or toluene and compounds comprising 8 carbon atoms or more, comprising at least one "reformate" distillation column (C1), an aromatics extraction unit (P1), a para-xylene separation unit (P2), a xylene isomerization unit (P3) and a transalkylation unit (P4), the separation device also comprising a purification column (C6) and toluene column (C10) for the distillation of effluents of the aromatics extraction unit (P1), the para-xylene separation unit (P2), the xylene isomerization unit (P3) and the transalkylation unit (P4),
in which at least one of the "reformate" distillation column (C1), the purification column (C6) and the toluene column (C10) is suitable for being operated under vacuum so that:
the majority of the compounds comprising 7 carbon atoms or less are recovered in the top of the column operated under vacuum, and
the majority of the compounds comprising 8 carbon atoms or more are recovered in the product at the bottom of the column operated under vacuum, and
the device further comprising an additional column, downstream of the outlet at the top of the column operated under vacuum, for bleeding off out of the separation device a vapour stream at the top of the column.

9. The device according to claim 8, in which the at least one of the distillation columns is adapted so that the product at the bottom of the distillation column operated under vacuum has a content of greater than 25% by weight of compounds comprising 8 carbon atoms and/or compounds of which the normal boiling point is less than 150° C.

10. The device according to claim 8, in which the at least one of the distillation columns is adapted so that the pressure at the column top of the distillation column operated under vacuum is between 0.03 MPa and 0.095 MPa.

11. The device as claimed in claim 8, in which the at least one of the distillation columns is adapted so that the reboiler of the distillation column operated under vacuum is operated at a temperature of less than 180° C.

12. The device according to claim 8, in which the at least one of the distillation columns is adapted so that the C4− content in the product at the top of the distillation column operated under vacuum is less than 1 mol %.

13. The device according to claim 8, in which the additional column is adapted so that the reboiler of the additional column is operated at a temperature of less than 180° C.

14. A process for separating a feedstock comprising benzene and/or toluene and compounds comprising 8 carbon atoms or more, in a separation device comprising at least one "reformate" distillation column (C1), an aromatics extraction unit (P1), a para-xylene separation unit (P2), a xylene isomerization unit (P3) and a transalkylation unit (P4), the effluents from the aromatics extraction unit (P1), the para-xylene separation unit (P2), the xylene isomerization unit (P3) and the transalkylation unit (P4) being separated in at least one of a purification column (C6), a deheptanizer (C7) and a toluene column (C10), in which at least one of the "reformate" distillation column (C1), the purification column (C6), the deheptanizer (C7) and the toluene column (C10) comprises a reboiler that is operated at a temperature of less than 150° C. and is operated under vacuum, the majority of the compounds comprising 7 carbon atoms or less are recovered in the top of the column operated under vacuum, and the majority of the compounds comprising 8 carbon atoms or more are recovered in the product at the bottom of the column operated under vacuum.

15. A device for separating a feedstock comprising benzene and/or toluene and compounds comprising 8 carbon atoms or more, the device comprising at least one "reformate" distillation column (C1), an aromatics extraction unit (P1), a para-xylene separation unit (P2), a xylene isomerization unit (P3) and a transalkylation unit (P4), the effluents from the aromatics extraction unit (P1), the para-xylene separation unit (P2), the xylene isomerization unit (P3) and the transalkylation unit (P4) being separated in at least one of a purification column (C6), a deheptanizer (C7) and a toluene column (C10), in which at least one of the "reformate" distillation column (C1), the purification column (C6), the deheptanizer (C7) and the toluene column (C10) comprises a reboiler that is configured to be operated at a temperature of less than 150° C. and is configured to be operated under vacuum so that:

the majority of the compounds comprising 7 carbon atoms or less are recovered in the top of the column operated under vacuum, and the majority of the compounds comprising 8 carbon atoms or more are recovered in the product at the bottom of the column operated under vacuum.

* * * * *